United States Patent
Ota et al.

(10) Patent No.: US 10,711,294 B2
(45) Date of Patent: Jul. 14, 2020

(54) NUCLEIC ACID ANALYSIS DEVICE

(71) Applicant: HITACHI HIGH-TECHNOLOGIES CORPORATION, Tokyo (JP)

(72) Inventors: Yuichiro Ota, Tokyo (JP); Tomohiro Shoji, Tokyo (JP); Toru Yokoyama, Tokyo (JP); Masatoshi Narahara, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 338 days.

(21) Appl. No.: 15/533,087

(22) PCT Filed: Dec. 26, 2014

(86) PCT No.: PCT/JP2014/084584
§ 371 (c)(1),
(2) Date: Jun. 5, 2017

(87) PCT Pub. No.: WO2016/103473
PCT Pub. Date: Jun. 30, 2016

(65) Prior Publication Data
US 2017/0362634 A1 Dec. 21, 2017

Related U.S. Application Data (60) Provisional application No. PCT/JP2014/084584, filed on Dec. 26, 2014.

(51) Int. Cl.
*C12Q 1/68* (2018.01)
*G01B 11/00* (2006.01)
(Continued)

(52) U.S. Cl.
CPC ............ *C12Q 1/68* (2013.01); *C12Q 1/6837* (2013.01); *G01B 11/00* (2013.01); *G01N 21/05* (2013.01);
(Continued)

(58) Field of Classification Search
CPC ................. G01N 2035/00158; C12Q 1/68
See application file for complete search history.

(56) References Cited

U.S. PATENT DOCUMENTS

| 2003/0152255 A1 | 8/2003 | Kira et al. |
| 2009/0270273 A1 | 10/2009 | Burns et al. |

(Continued)

FOREIGN PATENT DOCUMENTS

| JP | 2003-307518 A | 10/2003 |
| JP | 2013-527848 A | 7/2013 |

(Continued)

OTHER PUBLICATIONS

Jay Shendure et al., "Accurate Multiplex Polony Sequencing of an Evolved Bacterial Genome", Science, vol. 309, Sep. 9, 205, pp. 1728-1732.

(Continued)

*Primary Examiner* — Jonathan M Hurst
(74) *Attorney, Agent, or Firm* — Mattingly & Malur, PC (57) ABSTRACT

The substrate 100 for use in the analysis of a nucleic acid according to the present invention has multiple analysis areas 12 which are partitioned on a substrate 10, and enables the measurement of the analysis areas 12 while interchanging the analysis areas 12 in turn, said substrate 100 being characterized in that each of the analysis areas 12 consists of an adsorption part 13 onto which a DNA fragment or a carrier having the DNA fragment carried thereon can be adsorbed and a non-adsorption part 14 which is a part outside of the adsorption part 13, and the non-adsorption part 14 has, formed on at least a part thereof, a marker part 15 that has a specified shape and helps to identify the positions of the analysis areas 12.

2 Claims, 8 Drawing Sheets

(51) Int. Cl.
*C12Q 1/6837* (2018.01)
*G01N 21/05* (2006.01)
*G01N 21/64* (2006.01)
*G01N 35/00* (2006.01)

(52) U.S. Cl.
CPC . *G01N 21/6428* (2013.01); *G01N 2021/6439* (2013.01); *G01N 2035/00158* (2013.01)

(56) References Cited

U.S. PATENT DOCUMENTS

2010/0111768 A1* 5/2010 Banerjee ............. C12Q 1/6869
422/82.08
2011/0268347 A1 11/2011 Staker
2015/0176070 A1 6/2015 Ota et al.

FOREIGN PATENT DOCUMENTS

| | | |
|---|---|---|
| JP | 2013-150568 A | 8/2013 |
| JP | 2014-020832 A | 2/2014 |
| WO | 2014/148419 A1 | 9/2014 |

OTHER PUBLICATIONS

International Search Report of PCT/JP2014/084584 dated Mar. 24, 2015.

* cited by examiner

FIG. 11

NUCLEIC ACID ANALYSIS DEVICE

TECHNICAL FIELD

The present invention relates to a substrate for use in analysis of nucleic acid, a flow cell for use in analysis of nucleic acid, and a nucleic acid analysis device.

BACKGROUND ART

In recent years, as a method of analyzing base sequences of nucleic acid, there is known a method of concurrently analyzing base sequences of multiple DNA fragments. In this method, an absorbent portion capable of absorbing DNA fragments or the like and a non-absorbent portion not capable of the DNA fragment are formed on a substrate, for example, by photolithography or an etching technique. Then, DNA fragments or the like serving as an analysis target are absorbed in the absorbent portion to perform the analysis (for example, see PTL 1).

In the analysis method described above, excitation light is irradiated onto an analysis area including multiple DNA fragments where fluorochrome-labelled matrices corresponding to bases are introduced, and fluorescence emitted from each DNA fragment is detected to determine the base (for example, see NPL 1).

In this analysis method, typically, a plurality of analysis areas are provided on a single substrate, and the analysis is performed for overall analysis areas by changing the analysis area whenever the irradiation is performed. Then, a new fluorochrome-labelled matrix is introduced on the basis of a polymerase extension reaction, and each analysis area is analyzed through the aforementioned operation. By repeating this procedure, it is possible to effectively determine the base sequence.

CITATION LIST

Patent Literature

PTL 1: US 2009/0270273 A1
NPL 1: Science, 2005, Vol. 309, Pages 1728 to 1732

SUMMARY OF INVENTION

Technical Problem

However, in the background art described above, when the same analysis area is repeatedly analyzed, a positional deviation may occur in the analysis area at every cycle. This positional deviation makes it difficult to map the DNA fragments in every cycle, so that it may be difficult to obtain a suitable base sequence.

In view of the aforementioned problems, the present invention provides a substrate for use in analysis of nucleic acid, a flow cell for use in analysis of nucleic acid provided with this substrate for use in analysis of nucleic acid, and a nucleic acid analysis device, capable of reproducibly obtaining a position of the analysis area even when the positioning is performed repeatedly for the same analysis area.

Solution to Problem

The invention to solve the above issue is a substrate for use in analysis of nucleic acid having a plurality of analysis areas partitioned on a substrate to perform measurement by sequentially changing each analysis area,
wherein the analysis area has an absorbent portion capable of absorbing a DNA fragment or a vector where the DNA fragment is borne and a non-absorbent portion other than the absorbent portion, and
a marker portion having a predetermined shape to calculate a position of the analysis area is provided in at least a part of the non-absorbent portion.

Furthermore, another invention to solve the above issue is a flow cell for use in analysis of nucleic acid including:
the substrate for use in analysis of nucleic acid;
a light-transmitting cover placed to face the substrate for use in analysis of nucleic acid to transmit light;
a plurality of spacers provided between the substrate for use in analysis of nucleic acid and the light-transmitting cover and separated substantially in parallel with each other;
a flow passage formed in a portion interposed between the neighboring spacers between the substrate for use in analysis of nucleic acid and the light-transmitting cover to circulate a fluid;
an inlet port opened in one end of the flow passage to inject the fluid; and
an outlet port opened in the other end opposite to the inlet port of the flow passage to discharge the fluid.

In addition, another invention to solve the above issue is a nucleic acid analysis device including:
the flow cell for use in analysis of nucleic acid;
a circulation unit that circulates a fluid in a flow passage of the flow cell for use in analysis of nucleic acid;
a temperature control unit that controls a reactive temperature of the DNA fragment;
an irradiation unit that irradiates excitation light onto an analysis area serving as an analysis target through the light-transmitting cover;
a detection unit that detects fluorescence emitted from the DNA fragment by irradiating the excitation light using the light-transmitting cover and detects a position of the marker portion in the analysis area from the detected fluorescence; and
a carriage unit that carries the flow cell for use in analysis of nucleic acid and shifts the analysis area to a predetermined position with respect to the marker portion.

Note that, herein, a "predetermined shape" refers to a predefined shape (such as a cross shape) as seen in a plan view, used to determine a position inside the analysis area. In addition, herein, a "predetermined position" refers to a predefined position where the analysis area as an analysis target is shifted. Furthermore, herein, "a plurality of spacers" conceptually include a spacer provided with a single member such as a blanked sheet on which a plurality of spacers are formed by punching as well as a spacer provided with a plurality of members.

Advantageous Effects of Invention

According to the present invention, it is possible to provide a substrate for use in analysis of nucleic acid, a flow cell for use in analysis of nucleic acid having the substrate for use in analysis of nucleic acid, and a nucleic acid analysis device, capable of reproducibly obtaining a position of the analysis area even when the positioning is repeatedly performed for the same analysis area.

BRIEF DESCRIPTION OF DRAWINGS

FIGS. 5(a) to 5(c) are schematic diagrams illustrating a state that the fluorescent image obtained from the substrate for use in analysis of nucleic acid of FIG. 4 is distorted, in which

FIGS. 6(a) to 6(f) are schematic diagrams illustrating a method of manufacturing the substrate for use in analysis of nucleic acid of FIG. 1, in which

FIGS. 10(a) to 10(c) are schematic diagrams illustrating an exemplary analysis method using the nucleic acid analysis device according to the present invention, in which

DESCRIPTION OF EMBODIMENTS

<Substrate for Use in Analysis of Nucleic Acid>

A substrate for use in analysis of nucleic acid according to the present invention has a plurality of analysis areas partitioned on a substrate, so that measurement is performed by sequentially changing each analysis area. The analysis area includes an absorbent portion capable of absorbing a DNA fragment or a vector where the DNA fragment (hereinafter, the DNA fragment and the vector will be collectively referred to as an "analysis sample") is borne and a non-absorbent portion other than the absorbent portion. The non-absorbent portion has a marker portion having a predetermined shape for obtaining a position of the analysis area in at least a part thereof.

Substrates for use in analysis of nucleic acid according to first to fourth embodiments of the present invention will now be described with reference to the accompanying drawings. The present invention is not limited to the first to fourth embodiments and relating drawings.

First Embodiment

Figure 1:
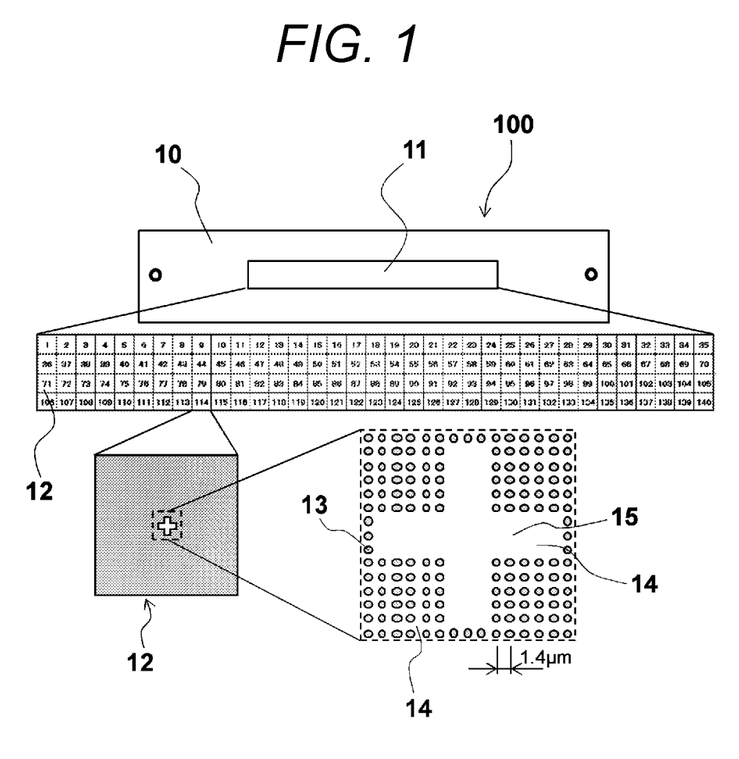
FIG. 1 is a schematic plan view illustrating a substrate for use in analysis of nucleic acid according to a first embodiment of the present invention.

FIG. 1 is a schematic plan view illustrating the substrate for use in analysis of nucleic acid according to the first embodiment of the present invention. As illustrated in FIG. 1, the substrate for use in analysis of nucleic acid 100 according to this embodiment substantially includes a substrate 10, a reaction area 11, an analysis area 12, an absorbent portion 13, and a non-absorbent portion 14. Note that, in FIG. 1, the reaction area 11, the analysis area 12, and a marker portion 15 (which will be described below) on the substrate 10 are enlargedly illustrated in a hierarchical manner.

The substrate 10 is a plate-like base material having the reaction area 11 formed on its one surface. This substrate 10 may include a plate having a hydrophobic thin film on its surface, such as a quartz plate, a silicon plate, and a synthetic resin plate. The reaction area 11 is partitioned into a plurality of analysis areas 12 as described below. Note that, in this embodiment, the reaction area 11 is partitioned into one hundred forty analysis areas 12.

The analysis area 12 is an area for absorbing an analysis sample s. The analysis area 12 includes a plurality of absorbent portions 13 capable of absorbing the analysis sample s and a non-absorbent portion 14 other than the absorbent portions 13.

The absorbent portion 13 is formed of a hydrophilic membrane or the like laminated on the substrate 10 and exposed to the surface in order to allow absorption of the analysis samples s. This hydrophilic membrane may include, for example, a film of inorganic oxide or the like into which a functional group capable of fixing the analysis sample s (such as an amino group) is introduced. This specific inorganic oxide may include, for example, aminosilane.

As illustrated in FIG. 1, each analysis area 12 has a plurality of absorbent portions 13 having a circular shape as seen in a plan view, and each absorbent portion 13 is arranged in a grid-like manner. In this manner, since each analysis area 12 has a plurality of absorbent portions 13, and each absorbent portion 13 is arranged in a grid-like manner, it is possible to easily and reliably recognize positions of the absorbent portions 13 within the analysis area 12.

Note that the absorbent portion 13 typically has a diameter of 0.01 to 10 μm as seen in a plan view. A lower limitation of this diameter is preferably set to 0.05 μm, more preferably 0.1 μm, and most preferably 0.2 μm in terms of easiness in formation of the absorbent portion 13 and improvement of absorbance of the analysis sample. Meanwhile, an upper limitation of the diameter is preferably set to 5 μm, more preferably 1 μm, and most preferably 0.5 μm in terms of improvement of an arrangement density of the absorbent portion 13.

The diameter of the absorbent portion 13 as seen in a plan view is preferably set depending on a spatial resolution (pixel dimension) of a detection unit of the nucleic acid analysis device provided with this substrate for use in analysis of nucleic acid 100. In this case, the diameter is preferably set to one pixel in terms of improvement of the arrangement density of the absorbent portion 13.

A pitch of the absorbent portion 13 is typically set to 0.05 to 50 μm. A lower limitation of the pitch is preferably set to 0.1 μm, more preferably 0.5 μm, and most preferably 1 μm in terms of improvement of an anti-interference property between the absorbent portions 13 neighboring in the analysis. Meanwhile, an upper limitation of the pitch is preferably set to 10 µm, more preferably 5 µm, and most preferably 2 µm in terms of improvement of the arrangement density of the absorbent portion 13.

Similar to the diameter, the pitch of the absorbent portion 13 is preferably set depending on a spatial resolution (pixel dimension) of a detection unit of the nucleic acid analysis device. In this case, the pitch is preferably set to four to five pixels, and more preferably five pixels in terms of the fluorescence resolution and improvement of the arrangement density of the absorbent portion 13.

The non-absorbent portion 14 includes a hydrophobic membrane laminated on the substrate 10 to prevent absorption of the analysis sample s. A compound for forming this hydrophobic membrane may include, for example, a multivalent organic compound, a carboxylic acid compound, a phosphate compound, a sulfate compound, a nitryl compound, and salts thereof. Note that the compound may be employed solely or as a combination of two or more compounds.

The non-absorbent portion 14 has a marker portion 15 having a cross shape for computing a position of the analysis area 12 in its part. Since a DNA fragment capable of emitting fluorescence is not easily absorbed in this marker portion 15, the marker portion 15 can be easily distinguished from the absorbent portion 13 using a fluorescent image of the analysis area 12.

Next, positioning of the analysis area 12 using the substrate for use in analysis of nucleic acid 100 according to the first embodiment will be described.

If the substrate for use in analysis of nucleic acid 100 is employed, and excitation light emitting a particular wavelength is irradiated onto the analysis area 12 including the absorbent portion 13 absorbed with the DNA fragment (analysis sample) where a fluorochrome-labelled matrix corresponding to the base is introduced, fluorescence is emitted from an absorbent portion 13 where a particular dye excited by this excitation light exists (hereinafter, also referred to as a "particular absorbent portion"). Note that, for example, in the case of four color fluorescence detection (detection for four different types of fluorescence corresponding to four types of bases), a fluorescence probability caused by irradiation of excitation light having a particular wavelength in an arbitrary absorbent portion 13 becomes about 25%.

Here, since a marker portion 15 having a predetermined shape for obtaining a position of the analysis area 12 (no fluorescent portion) is provided in at least a part of the non-absorbent portion 14, the position of the analysis area 12 is determined by finding the marker portion 15 by searching the obtained fluorescent image. Then, the substrate for use in analysis of nucleic acid 100 is shifted on the basis of the determined position of the analysis area 12 to match this analysis area 12 with the fluorescent image range. As a result, it is possible to obtain a fluorescent image of the analysis area 12 serving as an analysis target.

In this manner, on the substrate for use in analysis of nucleic acid 100, at least a part of the non-absorbent portion 14 of the analysis area 12 has the marker portion 15 having a predetermined shape for obtaining a position of the analysis area 12. Therefore, even when the positioning is repeated, it is possible to reproducibly obtain the position of the analysis area 12. As a result, it is possible to reliably and rapidly analyze base sequences of DNA fragments.

Second Embodiment

Figure 2:
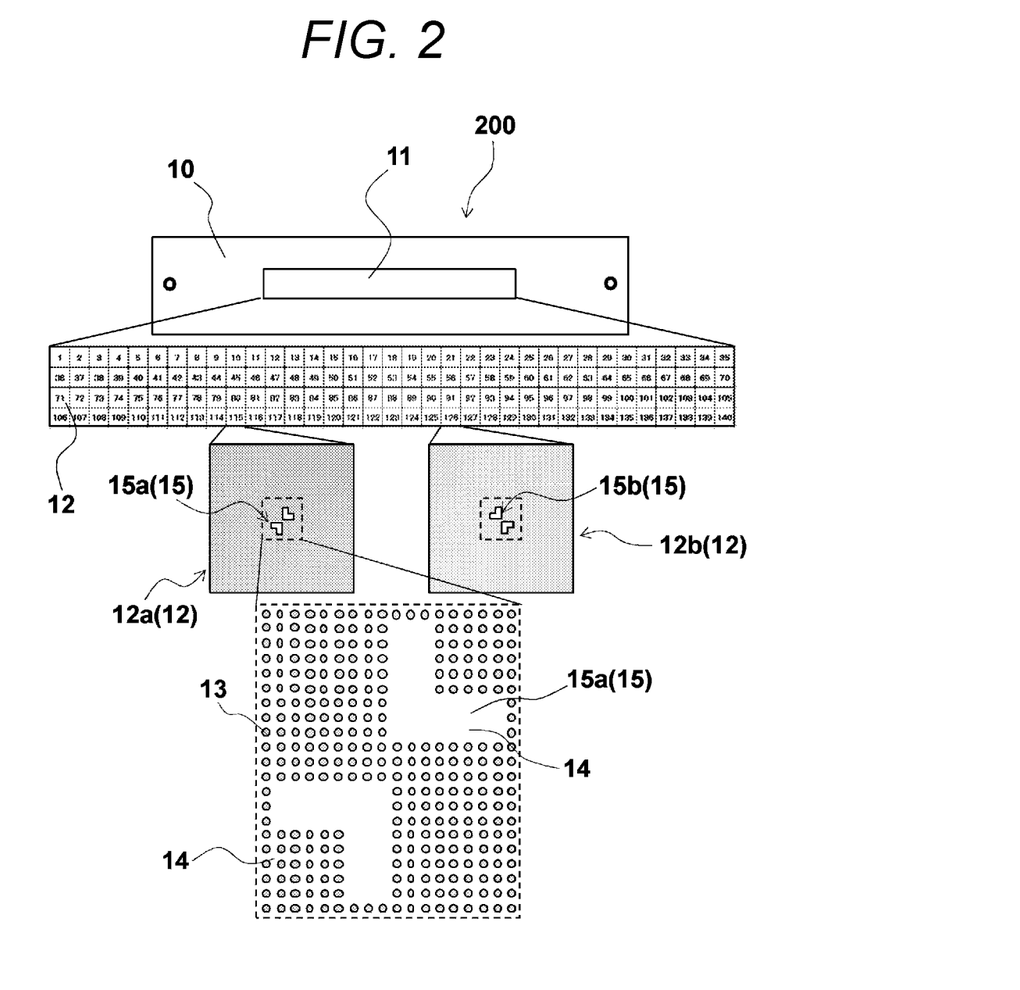
FIG. 2 is a schematic plan view illustrating a substrate for use in analysis of nucleic acid according to a second embodiment of the present invention.

FIG. 2 is a schematic plan view illustrating a substrate for use in analysis of nucleic acid according to a second embodiment of the present invention. As illustrated in FIG. 2, the substrate for use in analysis of nucleic acid 200 according to the second embodiment substantially includes a substrate 10, a reaction area 11, an analysis area 12, an absorbent portion 13, and a non-absorbent portion 14. The substrate for use in analysis of nucleic acid 200 according to the second embodiment is different from that of the first embodiment in that the shape of the marker portion 15 of the non-absorbent portion 14 as seen in a plan view is different depending on the analysis area 12. Note that the substrate 10, the reaction area 11, the analysis area 12, and the absorbent portion 13 are similar to those of the first embodiment. Therefore, like reference numerals denote like elements as in the first embodiment, and they will not be described repeatedly.

According to this embodiment, the shape of the marker portion 15 as seen in a plan view is different between at least the neighboring analysis areas 12. Specifically, as illustrated in FIG. 2, the substrate for use in analysis of nucleic acid 200 has two types of analysis areas 12a and 12b having different shapes of the marker portions 15 as seen in a plan view. The different types of analysis areas 12a and 12b are alternately arranged (the shape of the marker portion 15 is different between the odd-numbered analysis area 12a and the even-numbered analysis area 12b). In this embodiment, while the analysis area 12a has a marker portion 15a, the analysis area 12b has a marker portion 15b (refer to the shapes of the marker portions 15 in FIG. 2).

Next, positioning of the analysis area 12 using the substrate for use in analysis of nucleic acid 200 according to the second embodiment will be described.

If the substrate for use in analysis of nucleic acid 200 is employed, the shapes of the marker portions 15a and 15b of the odd-numbered analysis area 12a and the even-numbered analysis area 12b are stored in an external computer (not illustrated) in advance. Then, similar to the positioning of the first embodiment, the positioning is performed for the initial analysis area 12.

Then, detection of fluorescence is performed by irradiating excitation light. In this detection of fluorescence, the shape of the marker portion 15 is recognized when the fluorescent image of the target analysis area 12 is obtained. On the basis of the recognized shape, whether this analysis area 12 is the odd-numbered analysis area 12a or the even-numbered analysis area 12b is determined. For example, if the initial analysis area 12 is set as an odd number, the next analysis area 12 shifted after the analysis of the analysis area 12a recognizes the even-numbered marker portions 15b unless an erroneous operation such as misalignment occurs in a carriage unit (described below) of the substrate for use in analysis of nucleic acid 200. If the odd-numbered marker portion 15a is recognized instead of the even-numbered marker portion 15b, or if no fluorescence is detected from the obtained fluorescent image at all, this means that the corresponding area is not the target analysis area 12.

In this manner, the shape of the marker portion 15 on the substrate for use in analysis of nucleic acid 200 as seen in a plan view is different at least between the neighboring analysis areas 12. Therefore, it is possible to distinguish each analysis area 12 on the basis of the shape of the marker portion 15 and reliably analyze the target analysis area 12.

Note that the planar shape of the marker portion 15 is preferably different between overall analysis areas 12. Specifically, the shape of the marker portion 15 may include, for example, a numeric shape, a shape obtained by modeling a distinguishable symbol, or the like (not shown).

In this manner, since the planar shape of the marker portion 15 is different between overall analysis areas 12, it is possible to clearly distinguish each analysis area 12 on the basis of the shape of the marker portion 15 and more reliably analyze the target analysis area 12.

Third Embodiment

Figure 3:
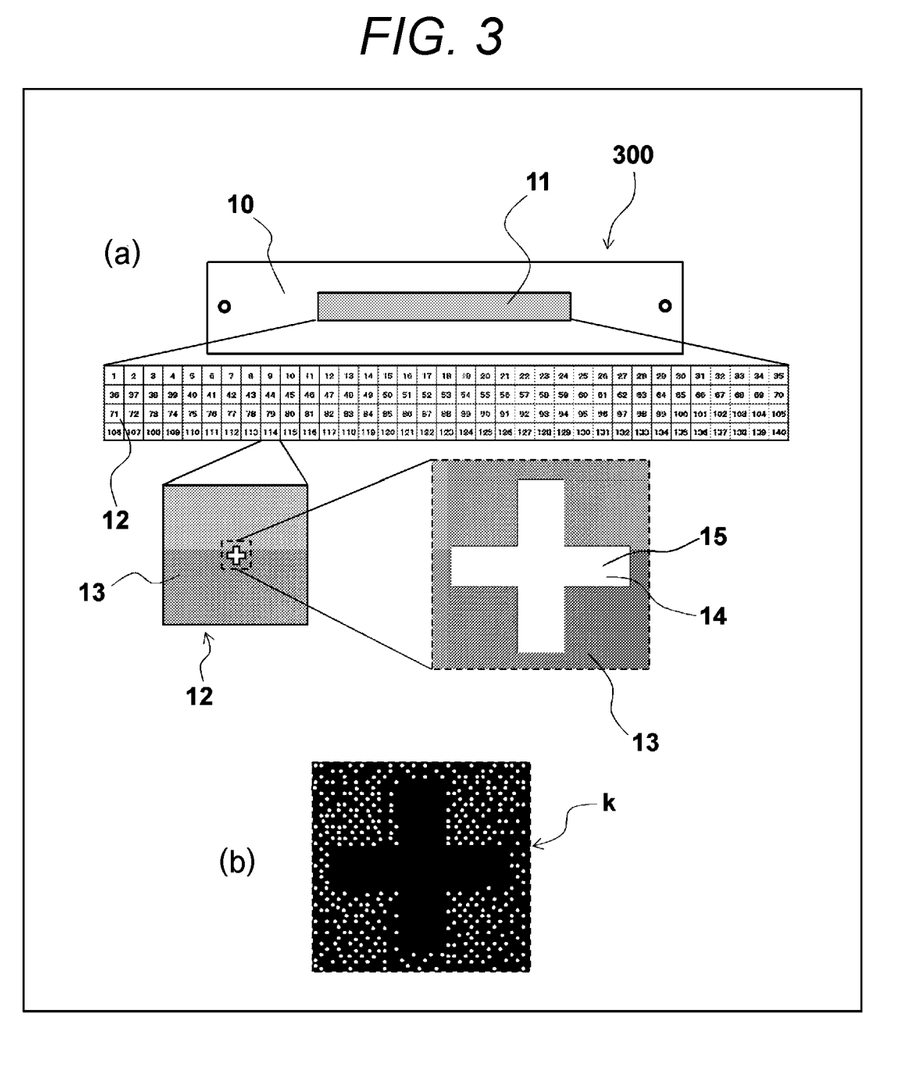
FIG. 3(a) is a schematic plan view illustrating a substrate for use in analysis of nucleic acid according to a third embodiment of the present invention.
FIG. 3(b) is a schematic diagram illustrating an exemplary fluorescent image.

FIGS. 3(a) and 3(b) are schematic diagrams illustrating a substrate for use in analysis of nucleic acid according to a third embodiment of the present invention. As illustrated in FIG. 3(a), the substrate for use in analysis of nucleic acid 300 according to the third embodiment substantially includes a substrate 10, a reaction area 11, an analysis area 12, an absorbent portion 13, and a non-absorbent portion 14. The substrate for use in analysis of nucleic acid 300 according to the third embodiment is different from that of the first embodiment in the absorbent portion 13 and the non-absorbent portion 14. Note that the substrate 10, the reaction area 11, and the analysis area 12 are similar to those of the first embodiment. Therefore, like reference numerals denote like elements as in the first embodiment, and they will not be described repeatedly. In addition, the positioning of the analysis area 12 using the substrate for use in analysis of nucleic acid 300 according to the third embodiment is similar to that of the first embodiment, and it will not also be described repeatedly.

According to this embodiment, the entire area of the non-absorbent portion 14 is the marker portion 15, and the remaining area of the analysis area 12 other than the marker portion 15 is the absorbent portion 13. Specifically, as illustrated in FIG. 3(a), the non-absorbent portion 14 having a cross shape and serving as the marker portion 15 is formed in an approximate center of the analysis area 12, and the entire remaining area of this analysis area 12 other than the non-absorbent portion 14 (marker portion 15) is the absorbent portion 13. Note that FIG. 3(b) illustrates an exemplary fluorescent image k obtained from the substrate for use in analysis of nucleic acid 300 according to this embodiment. In this drawing, white dots indicate portions corresponding to the analysis samples s emitting fluorescence.

In this manner, in the substrate for use in analysis of nucleic acid 300, the entire area of the non-absorbent portion 14 is the marker portion 15, and the remaining area of the analysis area 12 other than marker portion 15 is the absorbent portion 13. Therefore, it is possible to densely arrange the analysis sample s and analyze an amount of images at once.

Fourth Embodiment

Figure 4:
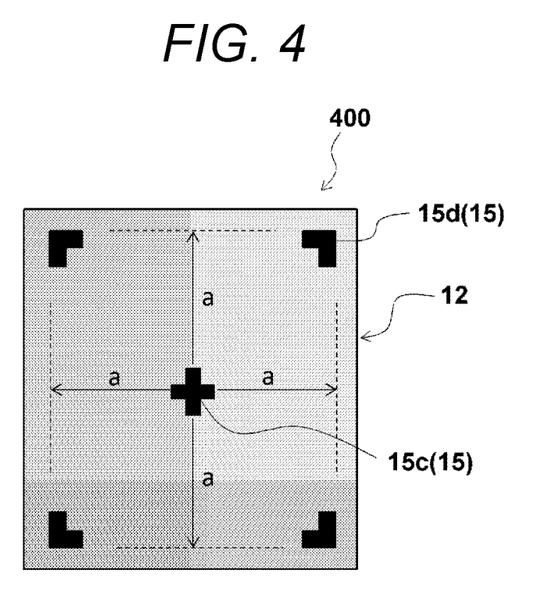
FIG. 4 is a schematic plan view illustrating a substrate for use in analysis of nucleic acid according to a fourth embodiment of the present invention, in which a single analysis area is enlargedly illustrated.

FIG. 4 is a schematic plan view illustrating a substrate for use in analysis of nucleic acid 400 according to a fourth embodiment of the present invention, in which a single analysis area 12 is enlargedly illustrated. The substrate for use in analysis of nucleic acid 400 according to the fourth embodiment substantially includes a substrate 10, a reaction area 11, an analysis area 12, an absorbent portion 13, and a non-absorbent portion 14. As illustrated in FIG. 4, the substrate for use in analysis of nucleic acid 400 according to the fourth embodiment is different from that of the first embodiment in that the marker portion 15 is arranged in each of four corners in addition to the center of the analysis area 12. Note that, since the substrate 10, the reaction area 11, and the analysis area 12 are similar to those of the first embodiment, they will not be described repeatedly. Furthermore, the absorbent portion 13 is similar to that of the first embodiment, and a plurality of absorbent portions 13 are not illustrated intentionally in FIG. 4 for simplicity purposes.

According to this embodiment, the marker portion 15 is used in positional correction of each absorbent portion 13 in the analysis area 12. Specifically, the substrate for use in analysis of nucleic acid 400 includes a marker portion 15c placed in the center of the analysis area 12 and L-shaped marker portions 15d provided in each of four corners of the analysis area 12. In addition, the marker portions 15d placed in the four corners are arranged such that straight lines obtained by linking the neighboring marker portions 15d of each corner are separated from the marker portion 15c placed in the center at the same distance "a." Furthermore, although not shown in the drawing, each absorbent portion 13 is arranged in a grid shape at an interval of five pixels on the analysis area other than the marker portion 15.

Next, positional correction of each absorbent portion 13 in the analysis area 12 using the substrate for use in analysis of nucleic acid 400 according to the fourth embodiment will be described with reference to FIGS. 5(a) to 5(c).

For example, positional correction of the absorbent portion 13 may be performed through the following method if a fluorescent image obtained from the substrate for use in analysis of nucleic acid 400 has a distortion. Specifically, as illustrated in FIG. 5(a), due to a distortion of the fluorescent image k1, a portion 15c' corresponding to the marker portion 15c in the center of the fluorescent image k1 (hereinafter, referred to as a "marker mapping portion 15c'") is separated from straight lines obtained by linking portions corresponding to the marker portions 15d in the neighboring corners (marker mapping portions 15d') at distances b, c, d, and e. In this case, as a method of estimating the position of the absorbent portion 13 in practice, for example, an interpolation technique such as a linear interpolation technique may be employed, in which interpolation is performed for each of the upper left, upper right, lower left, and lower right regions with respect to the marker mapping portion 15c'.

For example, as an example of such a linear interpolation method, an actual pitch is calculated by obtaining a proportion of the distance "a" (refer to FIG. 4) against each of the distance "b, c, d, and e" and multiplying the proportions by five pixels. Specifically, an actual pitch of the BD direction in the B-side region from the marker mapping portion 15c' in FIG. 5(a) becomes "b/a×five pixels." An actual pitch of the CE direction in the E-side region from the marker mapping portion 15c' becomes "e/a×five pixels." An actual pitch of the BD direction in the D-side region from the marker mapping portion 15c' becomes "d/a×five pixels." An actual pitch of the CE direction in the C-side region from the marker mapping portion 15c' becomes "c/a×five pixels." Using these values, positional correction of each absorbent portion 13 is performed.

Since a distortion of the fluorescent image depends on a detector of the nucleic acid analysis device, the aforementioned calculation may be performed only for the initial analysis area 12 of the first cycle. The correction is performed for the analysis areas 12 to be analyzed after using this calculation result. In addition, if two or more detectors are used in analysis, the calculation and the correction are performed in each detector.

Figure 5:
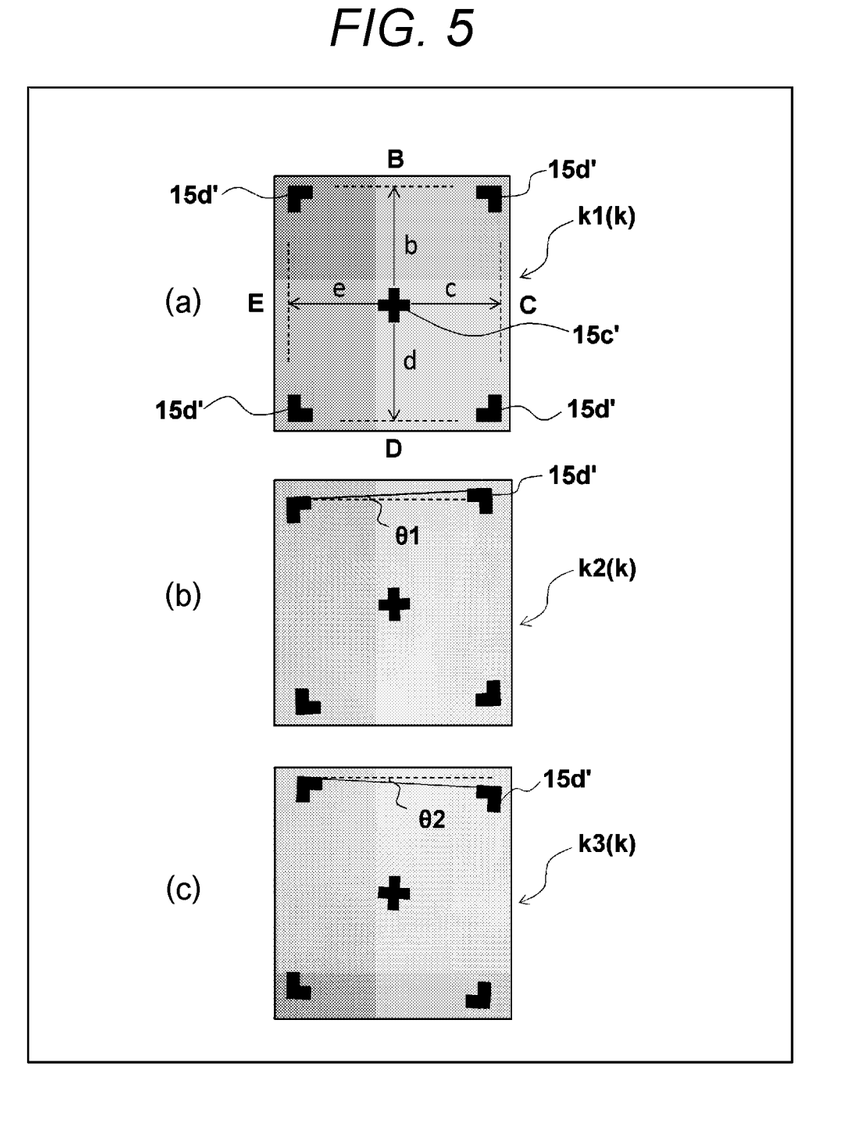
FIG. 5(a) shows a deformed state of fluorescent image.
FIG. 5(b) shows a rotated state of the fluorescent image.
FIG. 5(c) shows another rotated state of the fluorescent image.

Meanwhile, for a distortion (deviation) of the fluorescent image in the rotational direction with respect to the optical axis of the excitation light irradiated onto the substrate for use in analysis of nucleic acid 400, the positional correction of the absorbent portion 13 can be performed in the following way. Specifically, as illustrated in FIG. 5(b), an inclination θ1 is calculated from the marker mapping portion 15d' of the fluorescent image k2 obtained by the detector. Then, correction in the rotational direction is performed on the basis of the calculated inclination θ1. Note that, since the distortion of the rotational direction in the fluorescent image k depends on the detector of the nucleic acid analysis device, the aforementioned calculation may be performed only for the initial analysis area 12 of the first cycle, and the correction is performed for the analysis areas 12 to be analyzed after using this calculation result. In addition, if two or more detectors are used in the analysis, the calculation and the correction are performed in each detector. For example, FIG. 5(*c*) illustrates a fluorescent image k3 (inclination θ2) detected from another detector different from the aforementioned detector.

In this manner, since the marker portion 15 is used in positional correction of each absorbent portion 13 in the analysis area 12, it is possible to accurately recognize a position of each absorbent portion 13 in the analysis area 12.

<Method of Manufacturing Substrate for Use in Analysis of Nucleic Acid>

Figure 6:
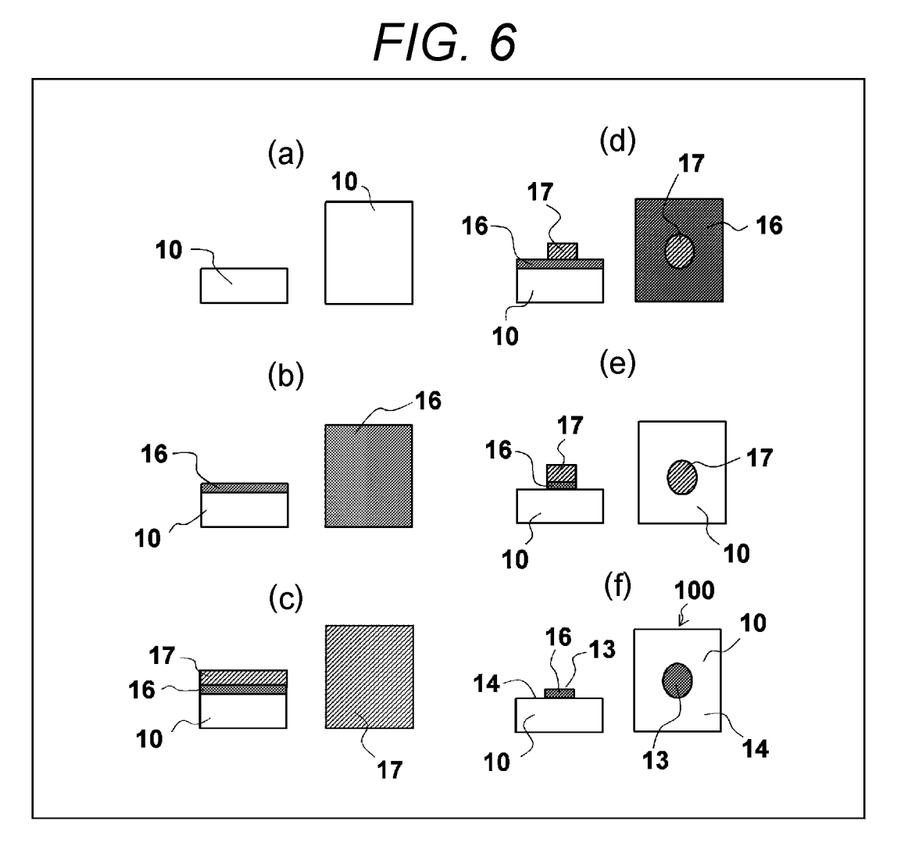
FIG. 6(a) shows a state before a hydrophilic membrane is formed.
FIG. 6(b) shows a state after a hydrophilic membrane is formed.
FIG. 6(c) shows a state after a resist film is formed.
FIG. 6(d) shows a state after development.
FIG. 6(e) shows a state after etching.
FIG. 6(f) shows a state after removal of the resist film.

Next, a method of manufacturing the aforementioned substrate for use in analysis of nucleic acid will be described. FIGS. 6(*a*) to 6(*f*) are schematic diagrams illustrating a method of manufacturing the substrate for use in analysis of nucleic acid 100 of FIG. 1. This substrate for use in analysis of nucleic acid 100 may be manufactured, for example, using a method described in JP 2011-99720 A. That is, a substrate 10 having one surface where a hydrophobic membrane is laminated in advance (refer to FIG. 6(*a*)) is prepared. On this hydrophobic membrane, a hydrophilic membrane 16 formed of specific inorganic oxide or the like is deposited, for example, through vacuum deposition, sputtering, chemic vapor deposition (CVD), physical vapor deposition (PVD), or the like (refer to FIG. 6(*b*)).

Then, a resist 17 is coated on the obtained hydrophilic membrane 16 (refer to FIG. 6(*c*)). Then, predetermined patterning is performed using a photolithographic technique (refer to FIG. 6(*d*)). An unnecessary part of the hydrophilic membrane is removed through etching by using the patterned resist 17 as a mask (refer to FIG. 6(*e*)), and the remaining resist 17 is removed by dissolving (refer to FIG. 6(*f*)). As a result, it is possible to manufacture a substrate for use in analysis of nucleic acid 100 having a desired absorbent portion 13 provided with the hydrophilic membrane 16. Note that, since the hydrophobic membrane is exposed on a part of the analysis area 12 other than the absorbent portion 13, this part serves as the non-absorbent portion 14.

<Flow Cell for Use in Analysis of Nucleic Acid>

The flow cell for use in analysis of nucleic acid according to the present invention includes the substrate for use in analysis of nucleic acid, a light-transmitting cover disposed to face the substrate for use in analysis of nucleic acid to transmit light, a plurality of spacers arranged between the substrate for use in analysis of nucleic acid and the light-transmitting cover and separated substantially in parallel with each other, a flow passage formed in a portion interposed by the neighboring spacers between the substrate for use in analysis of nucleic acid and the light-transmitting cover to circulate a fluid, an inlet port opened in one end of the flow passage to inject the fluid, and an outlet port opened in the other end opposite to the inlet port of the flow passage to discharge the fluid.

The flow cell for use in analysis of nucleic acid according to the present invention will now be described with the accompanying drawings. However, the present invention is not limited to the embodiments illustrated in the drawings.

Figure 7:
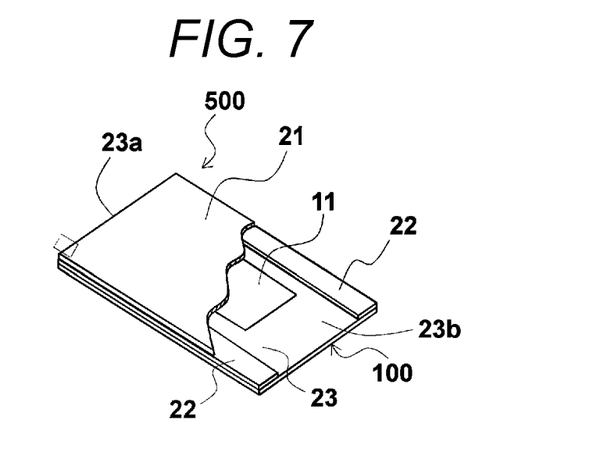
FIG. 7 is a schematic perspective view illustrating an exemplary flow cell for use in analysis of nucleic acid according to the present invention, in which the light-transmitting cover is partially cut away.

FIG. 7 is a schematic perspective view illustrating an exemplary flow cell for use in analysis of nucleic acid according to the present invention, in which the light-transmitting cover is partially cut away. As illustrated in FIG. 7, the flow cell for use in analysis of nucleic acid 500 substantially includes a substrate for use in analysis of nucleic acid 100, a light-transmitting cover 21, spacers 22, and a flow passage 23. Note that, since the substrate for use in analysis of nucleic acid 100 described above is employed as the substrate for use in analysis of nucleic acid in this embodiment, like reference numerals denote like element, and they will not be described repeatedly.

The light-transmitting cover 21 is a flat cover placed to face the substrate for use in analysis of nucleic acid 100 to transmit light. The light-transmitting cover may be formed of, for example, glass such as soda glass, quartz glass, or sapphire glass, light-transmitting resin such as transparent polyimide resin, or polycarbonate resin, and the like.

The spacers 22 are placed between the substrate for use in analysis of nucleic acid 100 and the light-transmitting cover 21 and are separated substantially in parallel with each other. The flow cell for use in analysis of nucleic acid 500 has a plurality of spacers 22. The spacers 22 may be formed of, for example, thermosetting or photosetting epoxy resin, acrylic resin, silicon resin, and the like as disclosed in JP 2006-87974 A. Out of these materials, in terms of improvement of a bonding strength with the glass or the light-transmitting resin, silicon resin is preferable, polysiloxane is more preferable, and polydimethylsiloxane (PDMS) is most preferable. In addition, the spacers 22 preferably have a thickness of 0.05 to 2 mm, and more preferably 0.2 to 1 mm, but not particularly limited thereto.

The flow passage 23 is a flow passage formed in a portion interposed between the neighboring spacers 22 between the substrate for use in analysis of nucleic acid 100 and the light-transmitting cover 21 to flow a fluid. For example, a fluid such as a reagent that can react with the DNA fragment flows through this flow passage 23. Specifically, the flow passage 23 is surrounded by the substrate for use in analysis of nucleic acid 100, the light-transmitting cover 21, and the spacers 22 to form a rectangular cross section as seen in the flow direction and a substantially rectangular parallel-piped space extending in the flow direction. The flow passage 23 has an inlet port 23*a* opened in one end to inject the fluid and an output port 23*b* opened in the other end opposite to the inlet port 23*a* to discharge the fluid.

In this manner, since the flow cell for use in analysis of nucleic acid 500 has the substrate for use in analysis of nucleic acid 100, it is possible to reproducibly obtain the position of the analysis area 12 even when positioning is repeatedly performed during the nucleic acid analysis. As a result, it is possible to reliably and rapidly analyze base sequences of DNA fragments.

<Method of Manufacturing Flow Cell for Use in Analysis of Nucleic Acid>

Next, a method of manufacturing the flow cell for use in analysis of nucleic acid 500 will be described. For the flow cell for use in analysis of nucleic acid 500, for example, a pair of spacers 22 are bonded to the substrate for use in analysis of nucleic acid 100 described above in parallel with each other using an adhesive. Then, the light-transmitting cover 21 is bonded to the bonded spacers 22 using an adhesive. Note that any type of adhesive may be employed without a particular limitation as long as it does not affect the nucleic acid analysis. Through the aforementioned process it is possible to manufacture the flow cell for use in analysis of nucleic acid 500 according to the present invention.

<Nucleic Acid Analysis Device>

The nucleic acid analysis device according to the present invention includes the flow cell for use in analysis of nucleic acid, a circulation unit that circulates the fluid in the flow passage of the flow cell for use in analysis of nucleic acid, a temperature control unit that controls an reactive temperature of the DNA fragment, an irradiation unit that irradiates excitation light onto the analysis area as an analysis target through the light-transmitting cover, a detection unit that detects the fluorescence emitted from the DNA fragment by irradiating the excitation light through the light-transmitting cover and detects a position of the marker portion in the analysis area from the detected fluorescence, and a carriage unit that carries the flow cell for use in analysis of nucleic acid and shifts the analysis area to a predetermined position with respect to the marker portion.

A nucleic acid analysis device according to the present invention will now be described with reference to the accompanying drawings. However, the present invention is not limited to the embodiments illustrated in the drawings.

Figure 8:
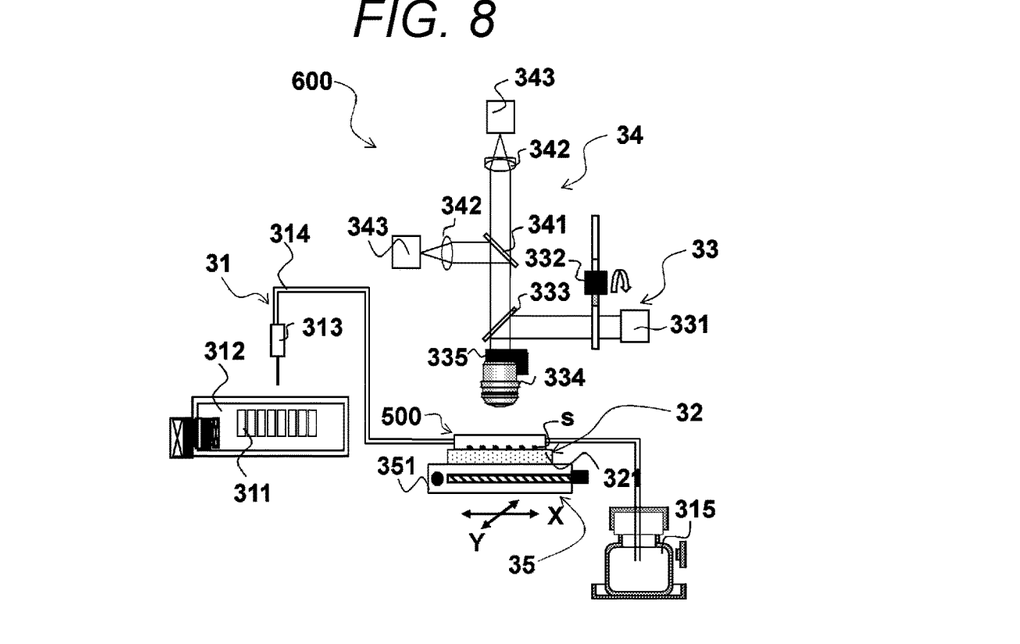
FIG. 8 is a schematic diagram illustrating an exemplary nucleic acid analysis device according to the present invention.
Figure 9:
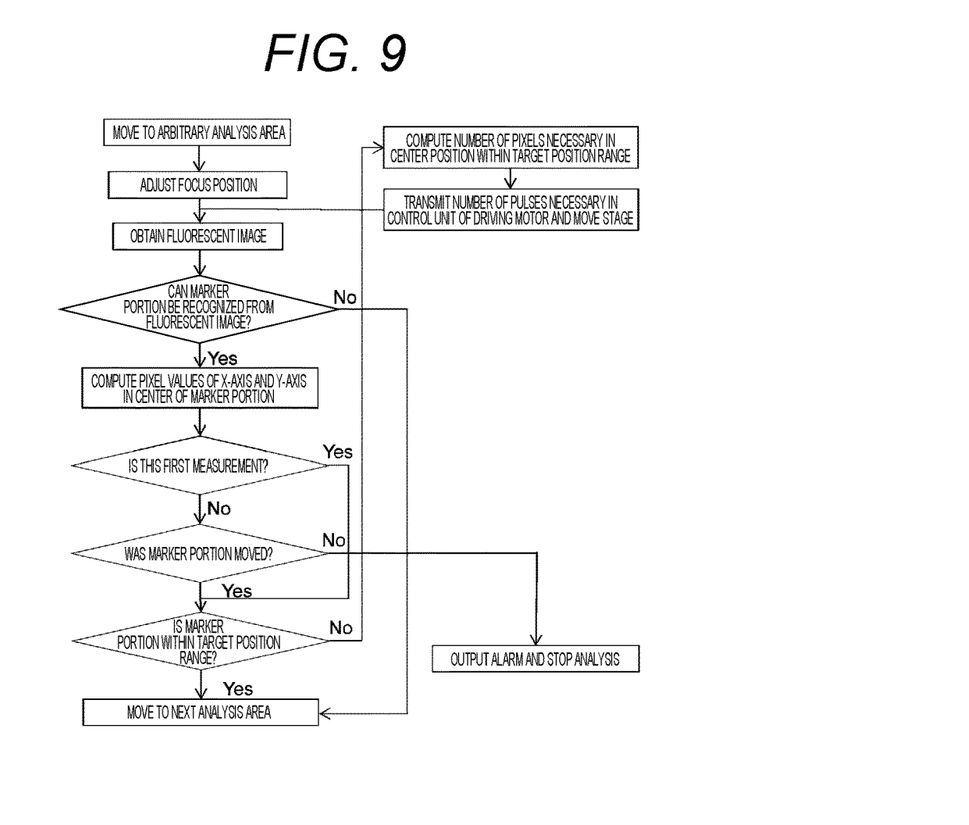
FIG. 9 is a flowchart illustrating a control process of the nucleic acid analysis device of FIG. 8.
Figure 10:
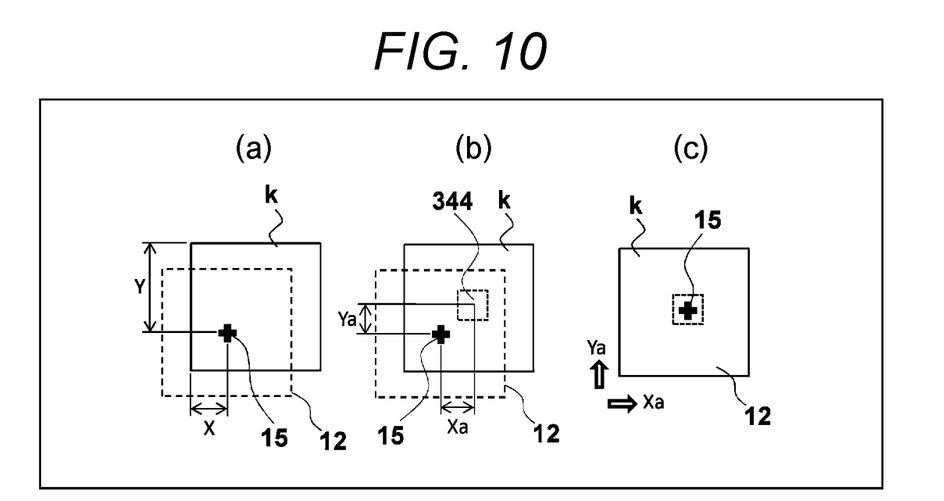
FIG. 10(a) shows a positional relationship of the marker portion in the fluorescent image before movement.
FIG. 10(b) shows a positional relationship between the target location range and the marker portion before movement.
FIG. 10(c) shows a positional relationship between the target location range and the marker portion after the movement.

FIG. 8 is a schematic diagram illustrating an exemplary nucleic acid analysis device according to the present invention. As illustrated in FIG. 8, the nucleic acid analysis device 600 substantially includes a flow cell for use in analysis of nucleic acid 500, a circulation unit 31, a temperature control unit 32, an irradiation unit 33, a detection unit 34, and a carriage unit 35. Note that the flow cell for use in analysis of nucleic acid 500 is similar to the flow cell for use in analysis of nucleic acid 500 described in the paragraph <Flow Cell for Use in Analysis of Nucleic Acid> described above. Therefore, like reference numerals denote like elements, and they will not be described repeatedly.

The circulation unit 31 circulates the fluid in the flow passage 23 of the flow cell for use in analysis of nucleic acid 500. The circulation unit 31 has a reagent cooling storage chamber 312 that houses a plurality of reagent containers 311 containing the reagent, a nozzle 313 that accesses the reagent container 311, a pipe 314 that introduces the reagent into the flow cell for use in analysis of nucleic acid 500, and a waste liquid reservoir 315 that disposes the reagent reacting with the DNA fragments.

The temperature control unit 32 controls a reaction temperature of the DNA fragment. The temperature control unit 32 has a temperature control substrate 321 provided on an XY-stage 351 described below to promote a reaction between the DNA fragment (analysis sample s) to be analyzed and the reagent. The temperature control substrate 321 is embedded with, for example, a peltier device.

The irradiation unit 33 has a light source 331 such as a light emitting diode (LED) serving as the excitation light, a filter switching mechanism 332 capable of selecting an arbitrary wavelength from the excitation light emitted from the light source 331, a dichroic mirror 333 that reflects the excitation light and transmits the fluorescence described below, an objective lens 334 that irradiates the excitation light onto the analysis sample s to be analyzed, and a Z-stage 335 that drives the objective lens 334 in the Z-axis direction perpendicular to both the X-axis and the Y-axis to adjust a focus of the excitation light.

The detection unit 34 detects the fluorescence emitted from the DNA fragment by irradiating the excitation light through the light-transmitting cover 21 and a position of the marker portion 15 in the analysis area 12 from the detected fluorescence. The detection unit 34 has an objective lens 334 that recovers the fluorescence emitted from the analysis sample s, a fluorescence separation dichroic mirror 341 that divides parallel light from the objective lens 334 on a wavelength basis, a tube lens 342 that focuses the parallel light, and a detector 343 provided with a sensor such as a complementary metal oxide semiconductor (CMOS) sensor for detecting the focused image. Note that, since the objective lens 334 of the detection unit 34 is shared with the irradiation unit 33, the same reference numerals are used.

The carriage unit 35 carries the flow cell for use in analysis of nucleic acid 500 and shifts the analysis area 12 to a predetermined position with respect to the marker portion 15. The carriage unit 35 has an XY-stage 351 capable of delivering the flow cell for use in analysis of nucleic acid in each of the X-axis and Y-axis directions coplanarly perpendicular to each other and a driving motor (not shown) that drives the XY-stage 351. Note that the XY-stage 351 is controlled in an open loop manner.

<Analysis Method>

Next, a method of analyzing base sequences of the DNA fragments using the nucleic acid analysis device 600 according to the present invention will be described with reference to FIGS. 8 to 11. Note that, here, a case where the analysis sample s is a vector that contains the DNA fragment, and the flow cell for use in analysis of nucleic acid 500 provided with the substrate for use in analysis of nucleic acid 100 according to the first embodiment described above is employed will be described by way of example.

The analysis using the nucleic acid analysis device 600 may be performed, for example, by combining processes described below, including "Preparation of Flow Cell," "Installation of Flow Cell," "Introduction of Reagent," "Temperature Control," "Shift of Stage," and "Positioning of Stage." While each process will be described in details hereinafter, the analysis using the nucleic acid analysis device 600 is not limited to the following aspects.

<Preparation of Flow Cell>

In this process, a flow cell for use in analysis of nucleic acid 500 (refer to FIG. 7) where the analysis sample s is borne in advance is prepared. The substrate for use in analysis of nucleic acid 100 of the flow cell for use in analysis of nucleic acid 500 has an absorbent portion 13 and a non-absorbent portion 14 in each analysis area 12 on the substrate 10, and a marker portion 15 having a cross shape is formed in the center of the non-absorbent portion 14 as illustrated in FIG. 1. Note that the analysis sample s is borne only in the absorbent portion 13.

<Installation of Flow Cell>

In this process, the flow cell for use in analysis of nucleic acid 500 prepared in the process <Preparation of Flow Cell> is fixed to the temperature control substrate 321 provided on the XY-stage 351 of the nucleic acid analysis device 600.

<Introduction of Reagent>

In this process, the nozzle 313 of the circulation unit 31 accesses the reagent container 311 of the reagent cooling storage chamber 312 to suction the reagent. Then, the suctioned reagent is injected into the flow passage of the flow cell for use in analysis of nucleic acid 500 through the pipe 314 and the inlet port 23a, and the injected reagent comes into contact with the analysis sample s borne in the absorbent portion to generate reaction. Note that the reagent subjected to the aforementioned reaction is disposed to the waste liquid reservoir 315 through the pipe.

<Temperature Control>

In this process, a temperature control is performed for the flow cell for use in analysis of nucleic acid 500 using the temperature control substrate 321 to allow the analysis sample s to have a predetermined temperature. Through this temperature control, the reagent reacts with the analysis sample s of the flow cell for use in analysis of nucleic acid 500. In this case, DNA elongation is performed by suitably repeating the aforementioned processes "Introduction of Reagent" and "Temperature Control." This elongation is performed by reacting polymerase with four types of nucleotide labeled with different fluorochromes. The nucleotide includes FAM-dCTP, Cy3-dATP, Texas Red-dGTP, or Cy5-dTsTP. The reagent contains polymerase, and only one base of complementary fluorescence nucleotide is incorporated into the DNA fragment.

<Shift of Stage>

In this process, in order to observe the reacted analysis sample s, the XY-stage 351 is driven by a driving motor (not shown) to shift the flow cell for use in analysis of nucleic acid 500 to a preset position. Here, the "preset position" refers to an initial target position of the analysis area 12 where the marker portion 15 is to be placed within a fluorescence detection range of the detection unit 34. Note that the accurate positioning of the stage will be described below in more details in the following paragraph "Positioning of Stage."

<Positioning of Stage>

In this process, first, a focus position of the analysis sample s in the objective lens 334 is adjusted by driving the Z-stage 335 of the detection unit 34. Then, after shifting the objective lens 334 to the focus position, excitation light having a particular wavelength is irradiated onto the analysis sample s using the filter switching mechanism 332. In this case, through the irradiation of excitation light, only an analysis sample s corresponding to an excitation wavelength out of the analysis samples s borne in the absorbent portion 13 emits fluorescence. Meanwhile, the marker portion 15 does not emit fluorescence.

Then, a fluorescent image k is obtained using the detection unit 34. In this case, for example, when the four colors of fluorescence described above are detected, the analysis sample s emits fluorescence with a probability of "¼." Therefore, it is possible to perceive a shape of the marker portion 15 that does not emit fluorescence out of the obtained fluorescent image k. Then, as illustrated in FIGS. 10(a) to 10(c), for the detection range of the fluorescent image k, a marker portion 15 having a shape stored in a computer (not shown) in advance is searched. In this case, if the marker portion 15 is searched, pixel values of the X-axis and the Y-axis in the center of the marker portion 15 (coordinates converted into pixels of the marker portion 15 in the fluorescent image k) are calculated (refer to FIG. 10(a)). If the marker portion 15 is not searched, the search area moves to the next analysis area by driving the XY-stage 351. Note that, if the calculated pixel value is within a target location range 344, the positioning of the XY-stage 351 is not performed. Meanwhile, if the calculated pixel value is out of the target location range 344, relative pixel numbers Xa and Ya for this pixel values for the center position within the target location range 344 are calculated (refer to FIG. 10(b)). Then, the pixel numbers Xa and Ya are converted into the number of pulses necessary in the positioning, and the number of pulses is transmitted to the carriage unit 35. After this transmission, the XY-stage 351 is moved by driving the driving motor of the carriage unit 35 (refer to FIG. 10(c)).

Then, irradiation of the excitation light and position detection of the marker portion 15 using the detection unit 34 are performed again to check whether or not the marker portion 15 is shifted to the target location range 344. In this case, if the marker portion 15 is within the target location range 344, the positioning of the XY-stage 351 is completed. Meanwhile, if the marker portion 15 is out of the target location range 344, the positioning is performed again. Then, after this positioning is completed, this position (the aforementioned number of pulses) is stored. Note that, if the position of the marker portion 15 does not change after the positioning of the XY-stage 351, it is considered as misalignment of the driving motor, and the analysis is interrupted by outputting an alarm.

<Detection of Fluorescence>

In this process, a focus position is adjusted by driving the objective lens 334 of the detection unit 34 again. Note that this re-adjustment of the focus position is performed to correct a deviation in the vertical direction caused by the movement of the XY-stage. However, if the detection unit 34 and the analysis samples have a sufficient depth of field, this adjustment is not necessary.

Then, using the filter switching mechanism 332, the excitation light is irradiated onto the analysis area 12 by switching the excitation light between two wavelength bands of 490 nm and 595 nm as a median, and the fluorescence is detected on each occasion. Here, the excitation light having a wavelength of 490 nm as a median is used to detect fluorescence of FAM-dCTP and Cy3-dATP, and the excitation light having a wavelength of 595 nm as a median is used to detect fluorescence of Texas Red-dGTP and Cy5-dTsTP.

The fluorescence emitted from the analysis sample 12 is input to a pair of detectors 343 through the fluorescence separation dichroic mirror 341. Here, since the fluorescence separation dichroic mirror 341 has a smooth reflection characteristic for the four color fluorescence wavelength regions, it is possible to calculate a ratio of the fluorescence intensity at a bright spot emitted from the analysis sample s using a pair of detectors 343. For this reason, by calculating an intensity ratio on the image planes of a pair of detectors 343, it is possible to determine which one of the four colors of fluorescence the fluorescence of the analysis sample s belongs to. Note that several ten thousands to several hundred thousands of analysis samples s are borne on the analysis sample 12, and which position of the analysis samples s emits which fluorescence is detected in a batch through the fluorescence detection.

Figure 11:
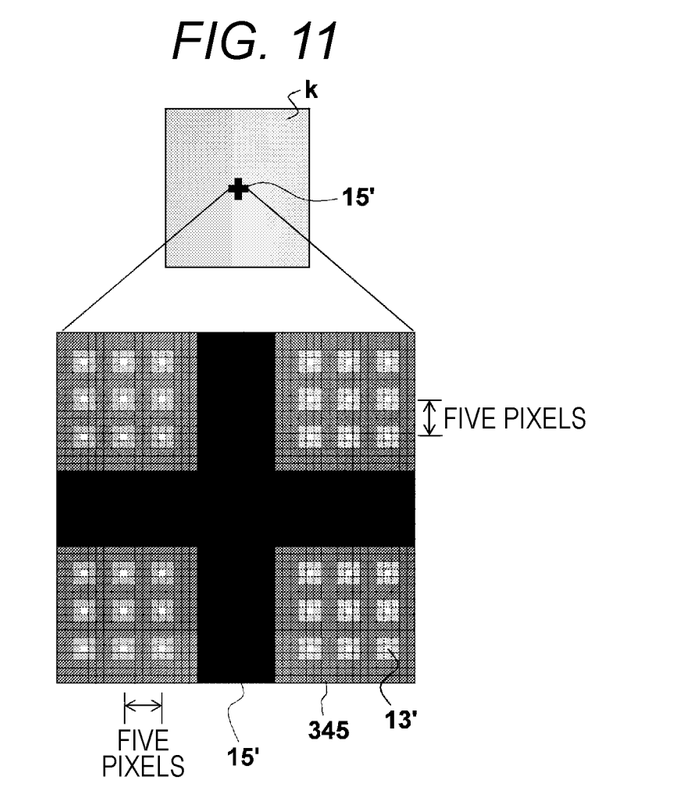
FIG. 11 is a schematic diagram illustrating an exemplary fluorescent image using the substrate for use in analysis of nucleic acid of FIG. 1.

Next, an exemplary fluorescent image k detected through the fluorescence detection is illustrated in FIG. 11. In FIG. 11, reference numeral "345" denotes pixels of the fluorescent image k, reference numeral "13'" denotes a portion on the fluorescent image k corresponding to the absorbent portion 13, and reference numeral "15'" denotes a portion on the fluorescent image k corresponding to the marker portion 15. FIG. 11 illustrates an exemplary fluorescent image when each absorbent portion 13 is arranged at an interval of 1.4 μm, a spatial resolution of the detection unit 34 is set to 0.28 μm/pixel, and the absorbent portion 13 is arranged at the same interval as five pixels of the fluorescent image k. In this example, the analysis sample s has a size of 0.28 μm or larger. For this reason, when the fluorescence of the analysis sample s is detected, a sample position is specified at an interval of five pixels from the edge of the marker portion 15, and fluorescence of nine pixels (three pixels in each direction) is detected for each position of each analysis sample s.

After completing the detection of fluorescence for a single analysis area 12, the detection range is shifted to the next analysis area 12. Then, the positioning on the XY-stage 351 is performed again, and fluorescence is detected from this analysis area 12. The movement of the XY-stage 351, the positioning of the analysis sample s, the storing of the position of the analysis sample s, and the fluorescence detection are repeated until detection is completed for all of the analysis areas 12. Note that, in order to reduce the analysis time, the positioning of the analysis sample s is performed only for an arbitrary analysis area 12, and the position information stored as described above may be used for the other analysis areas 12. Hereinbefore, an operation for a single cycle in this analysis has been described in brief.

Next, the analysis is performed for the second and subsequent cycles. In the stage movement of the second and subsequent cycles, the positioning is performed by shifting to the position of the initial analysis area 12 obtained in the positioning of the first cycle. This positioning is performed to correct thermal expansion caused by an internal temperature change of the nucleic acid analysis device 600. After this positioning is completed, the corrected position is stored.

For the subsequent analysis area 12, the analysis is performed by shifting to a relative position from the initial analysis area 12 obtained in the first cycle. For example, it is assumed that the initial analysis areas 12 of the first cycle and the subsequent two analysis areas 12 are positioned in 1,000 µm, 2,000 µm, and 3,000 µm, respectively. If the initial analysis area 12 of the second cycle is positioned in 950 µm, the next two analysis areas 12 are positioned in 1,950 µm and 2,950 µm.

Note that, in this operation, an error or a positional deviation may occur in accuracy of the repeated positioning of the XY-stage 351. If the accuracy of the repeated positioning of the XY-stage 351 is sufficiently low, a detection loss is not easily generated. However, if the accuracy of the repeated positioning of the XY-stage 351 is high, it is not negligible. If the accuracy of repeated positioning is high, it is necessary to increase the analysis areas 12 for the positioning considering the detection loss and the detection time.

By repeating the aforementioned cycles, the DNA base sequences of the analysis sample s are analyzed. For example, assuming that a certain analysis sample s emits fluorescence for each cycle in order of Cy3→Texas Red-→FAM→Cy5→ . . . , the base sequence of the sample can be determined as "A→G→C→T→ . . . " from the dNTP corresponding to the fluorochrome. In this manner, fluorescence is detected from several ten thousands to hundred thousands of analysis samples s in a batch, and all of the base sequences of the analysis samples s are determined in parallel.

Note that, although the analysis of the DNA base sequences of the analysis samples s starts from the first cycle in this example, the first cycle may be a mapping operation of the analysis area 12. In this mapping operation, if, for example, Texas Red-dGTP is incorporated into the DNA fragments of all of the analysis samples, all of the analysis samples emit fluorescence using excitation light having a wavelength of 595 nm. As a result, it is possible more reliably detect the marker portion. Therefore, it is possible to reduce the analysis area 12 where the positioning is not performed.

In this manner, the nucleic acid analysis device 600 has the flow cell for use in analysis of nucleic acid 500 provided with this substrate for use in analysis of nucleic acid 100. Therefore, even when the repeated positioning is performed, it is possible to reproducibly obtain the position of the absorbent portion 13. As a result, it is possible to reliably and rapidly analyze the base sequences of the DNA fragments.

Note that the substrate for use in analysis of nucleic acid, the flow cell for use in analysis of nucleic acid, and the nucleic acid analysis device according to the present invention are not limited to the embodiments described above, but the scope of the invention may encompass those described in the claims, their equivalents, and all possible changes.

For example, although the marker portion 15 has a cross shape or a hook shape by way of example in the aforementioned embodiments, any shape of the marker portion, such as a star shape or a circular shape, may be employed as long as the position of the marker portion 15 can be specified in the analysis area 12.

Although the substrate for use in analysis of nucleic acid 400 having the marker portions 15 formed in the center and the four corners of the analysis area 12 has been described in FIGS. 4 and 5(a) to 5(c), the scope of the invention may also include a substrate having no marker portion 15 in the center or having the marker portions 15 formed in only in opposite corners.

Although the flow cell for use in analysis of nucleic acid 500 provided with the substrate for use in analysis of nucleic acid 100 has been described in the aforementioned embodiments, any substrate for use in analysis of nucleic acid may also be employed as long as it satisfies the configuration of the substrate for use in analysis of nucleic acid according to the present invention.

Although the flow cell for use in analysis of nucleic acid 500 provided with a pair of spacers 22 separated substantially in parallel with each other has been described in FIG. 7, the flow cell for use in analysis of nucleic acid may have three or more spacers 22 to provide a plurality of lines of flow passages 23. For example, a flow cell for use in analysis of nucleic acid formed of polydimethylsiloxane (PDMS) or the like and provided with a blanked sheet obtained by blanking the flow passage portion may also be employed.

While the nucleic acid analysis device 600 provided with the flow cell for use in analysis of nucleic acid 500 has been described in the aforementioned embodiments, any flow cell for use in analysis of nucleic acid may also be employed as long as it satisfies a configuration of the flow cell for use in analysis of nucleic acid according to the present invention.

While the nucleic acid analysis device 600 having the detection unit 34 provided with a pair of detectors 343 has been described in FIG. 8, the nucleic acid analysis device may be additionally provided with a fluorescence separation dichroic mirror, and the nucleic acid analysis device may have the detection unit 34 having three or four detectors.

REFERENCE SIGNS LIST 10 substrate
11 reaction area
12 analysis area
13 absorbent portion
14 non-absorbent portion
15 marker portion
21 light-transmitting cover
22 spacer
23 flow passage
23a inlet port
23b outlet port
31 circulation unit
32 temperature control unit
33 irradiation unit
34 detection unit
35 carriage unit
100, 200, 300, 400 substrate for use in analysis of nucleic acid
500 flow cell for use in analysis of nucleic acid
600 nucleic acid analysis device
s analysis sample
k fluorescent image

The invention claimed is:

1. A nucleic acid analysis device comprising:
a flow cell for use in analysis of nucleic acid having a substrate,
 the substrate having a plurality of analysis areas partitioned on the substrate,
 each of the analysis areas having a plurality of absorbent portions capable of absorbing a DNA fragment or a vector where the DNA fragment is borne,
 at least one of the analysis areas having the plurality of absorbent portions and a non-absorbent portion other than the absorbent portions, and at least a part of the non-absorbent portion defines a first marker portion having a predetermined shape disposed at a center of the respective analysis area and plural second marker portions each having respective predetermined shapes and disposed at corners of the respective analysis area;
a piping connected to the flow cell to pass a fluid through a flow passage of the flow cell;
a temperature control device that controls a reactive temperature of the flow cell;
a light source that irradiates excitation light onto the at least one of the analysis areas serving as an analysis target;
a detection unit including a detector that detects fluorescence emitted from the analysis target by irradiating the excitation light thereon; and
a stage configured to support the flow cell and a driving motor configured to move the stage,
wherein, in each of the at least one of the analysis areas, straight lines obtained by linking the respective second marker portions are separated from the respective first marker portion by a same distance.

2. The nucleic acid analysis device according to claim 1, wherein the driving motor is configured to move the stage in each of X-axis and Y-axis directions which are coplanarly perpendicular to each other.

* * * * *